United States Patent [19]

Padjen et al.

[11] Patent Number: 4,719,922

[45] Date of Patent: Jan. 19, 1988

[54] STIMULATOR APPARATUS

[75] Inventors: Ante L. Padjen, Beaconsfield; Bruce MacDougall; Hans Schulze, both of Montreal, all of Canada

[73] Assignee: 147638 Canada Inc., Montreal, Canada

[21] Appl. No.: 835,285

[22] Filed: Mar. 3, 1986

[51] Int. Cl.⁴ ............................................... A61N 1/36
[52] U.S. Cl. ..................................... 128/421; 128/908
[58] Field of Search ................... 128/420 R, 421, 422, 128/423 R, 908

[56] References Cited

U.S. PATENT DOCUMENTS

| | | | |
|---|---|---|---|
| 3,523,539 | 8/1970 | Lavezzo et al. | 128/422 |
| 4,088,141 | 5/1978 | Niemi | 128/421 |
| 4,255,790 | 3/1981 | Hondeghem | 128/421 X |
| 4,582,063 | 4/1986 | Mickiewicz | 128/421 |

FOREIGN PATENT DOCUMENTS 0054654  6/1982  European Pat. Off. ............ 128/421

OTHER PUBLICATIONS

Goovaerts et al., "Accurate Isolated ... Applications", Med. & Biol. Eng. & Comput., 1981, 19, 4, 491–496.

Primary Examiner—Lee S. Cohen
Attorney, Agent, or Firm—Chilton, Alix & Van Kirk

[57] ABSTRACT

A stimulator apparatus for applying a low frequency pulse train, modulating a high frequency pulse train, to a patient includes electrodes for placement on the patient in the area of stimulation. A programmable microprocessor generates the pulse train and an electrode driver, to which the low frequency pulse train is fed, is connected to the electrodes. An electrode monitor is connected to an output of the electrode driver, and the output of the monitor is fed to an interrupt terminal of the microprocessor whereby to detect an unacceptable electrode connection. The apparatus also includes a display console including a display arrangement and a switch group. The electrode driver, in accordance with the invention, provides an adjustable constant current to the electrodes.

7 Claims, 10 Drawing Figures

STIMULATOR APPARATUS

BACKGROUND OF INVENTION

1. Field of the Invention

The invention relates to apparatus for nerve and/or muscle stimulation or cranial electrotherapy stimulation (CES). More specifically, the invention relates to such an apparatus which includes a programmable microprocessor for effecting control of the apparatus and for generating waveforms used in the operation of the apparatus. Even more specifically, the invention relates to such a stimulation apparatus which includes a novel electrode driver and monitor means.

2. Description of Prior Art

Apparatus of the general class of nerve and/or muscle stimulation are known in the art as illustrated, for example, in U.S. Pat. No. 3,902,502, Liss et al, Sept. 2, 1975, U.S. Pat. No. 4,084,595, Miller, Apr. 18, 1978, U.S. Pat. No. 4,121,594, Miller et al, Oct. 24, 1978, U.S. Pat. No. 4,147,171, Green et al, Apr. 3, 1979 and U.S. Pat. No. 4,148,321, Wyss et al, Apr. 10, 1979. From these patents, it is known to use a low frequency waveform modulated by a high frequency waveform. The high frequency waveform "breaks" the skin barrier, that is, it is able to penetrate through the capacitive effect of the skin as the capacitive effect of the skin presents a low impedance to a high frequency. The capacitive effect of the skin acts as a filter to the high frequency so that the nerves and/or muscles are stimulated only by the low frequency waveform. It is also known that a current pulse train should be used rather than a voltage pulse train, and, for example, the U.S. Pat. No. 3,902,502 teaches a source of constant current 20 for driving the electrodes. However, none of the patents teach an electrode driver of the same form and construction as per the present application.

Further examples of teachings in the art relating to the general class of nerve and/or muscle stimulation are given in U.S. Pat. No. 4,338,945, Hosugi et al, July 13, 1982, U.S. Pat. No. 4,088,141, Niemi, May 9, 1978, U.S. Pat. No. 4,398,537, Holmbo, Aug. 16, 1983, Canadian Pat. No. 1,175,493, Hepp et al, Oct. 2, 1984, Canadian Pat. No. 1,118,051, Keller Jr., Feb. 9, 1982, and Canadian Pat. No. 1,116,701, Hogfors et al, Jan. 19, 1982.

The U.S. Pat. No. 4,338,945 teaches a system for generating a randomized pulse train. The U.S. Pat. No. 4,088,141 teaches a system which is automatically disabled when a fault is detected. However, the detector and disabling are not similar to the teachings of the present application. The U.S. Pat. No. 4,398,537 is of interest in that it relates to an implanted nerve stimulator.

The Canadian Pat. No. 1,175,493 teaches a microprocessor based nerve stimulator. The Canadian Pat. No. 1,118,051 provides scanned output parameters, and the Canadian Pat. No. 1,116,701 teaches a stimulator with output signal controls.

None of the above references teach a stimulator wherein it is possible to apply a predetermined number of pulses, including a single pulse, by triggering the pulse train by an incoming trigger signal to the microprocessor.

SUMMARY OF INVENTION

It is an object of the invention to provide an apparatus for nerve and/or muscle stimulation which includes a microprocessor for effecting control of the apparatus and for generating waveforms used in the operation of the apparatus.

It is a further object of the invention to provide such a stimulation apparatus which includes a novel electrode driver and monitor means.

In accordance with the invention a stimulator apparatus for applying a low frequency pulse train, modulating a high frequency pulse train, to a patient includes electrode means for placement on the patient in the area of stimulation. Programmable microprocessor means generate the modulated high frequency pulse train and electrode driver means are connected, at the input thereof, to the modulating low frequency pulse train and, at the output thereof, to the electrode means. An electrode monitor has an input connected to the output of the electrode driver means and an output connected to an input terminal of the microprocessor means whereby to detect poor electrode connections. The apparatus also includes a display console including a display arrangement and a switch group. The electrode driver means provides an adjustable constant current to the electrode means.

BRIEF DESCRIPTION OF DRAWINGS

The invention will be better understood by an examination of the following description, together with the accompanying drawings, in which.

DESCRIPTION OF PREFERRED EMBODIMENTS

Figure 1:
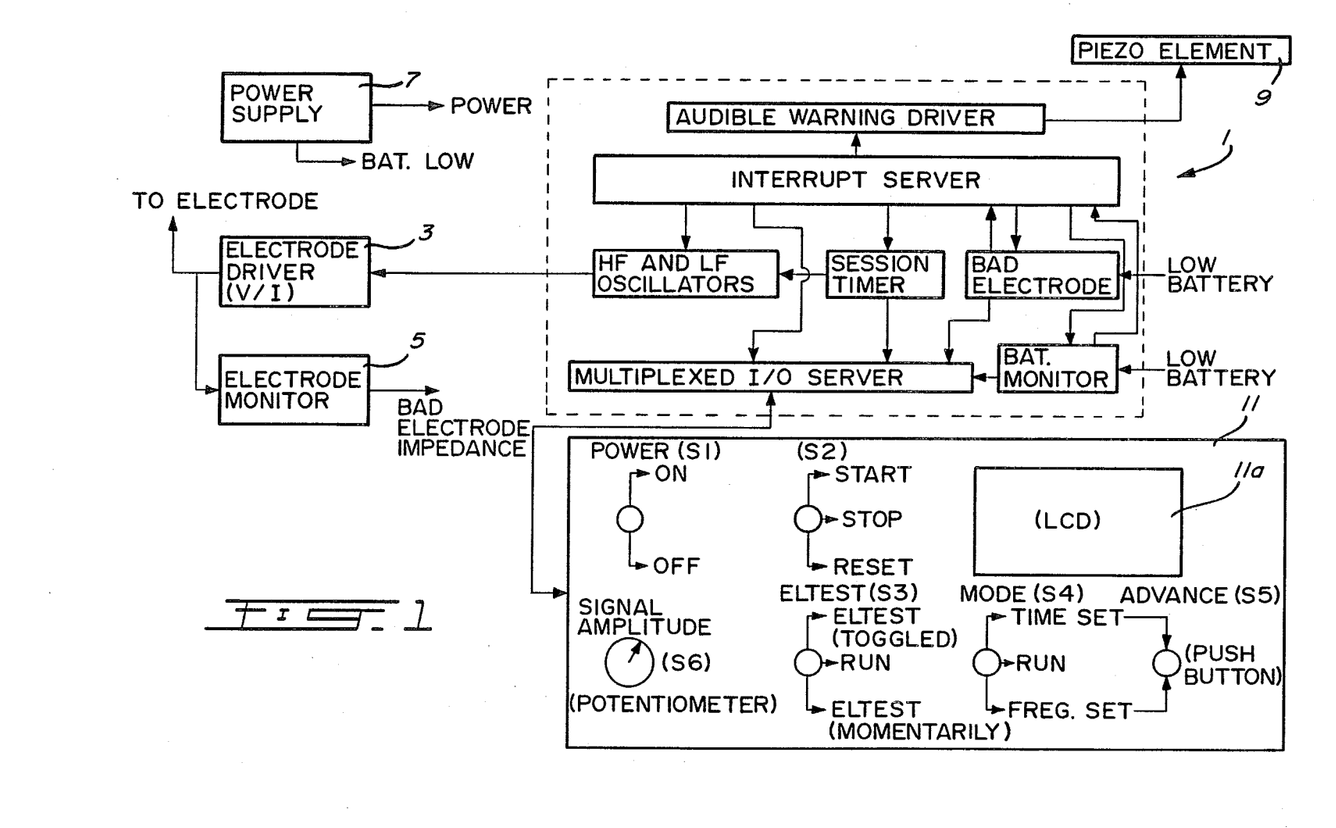
FIG. 1 is a block diagram of the system.

Referring to FIG. 1, the apparatus comprises a programmable microprocessor, in dotted lines, indicated generally at 1. The blocks within the microprocessor are not physical constructions, but rather, are indications of software programs which drive the microprocessor. Flow charts for these programs are discussed below.

The apparatus also includes an electrode driver 3, which is more fully described below and more fully illustrated in FIG. 2, and an electrode monitor 5, which is similarly more fully illustrated in FIG. 2. The apparatus is powered by a power supply 7 which may comprise a rechargeable battery.

The apparatus also includes a piezoelectric element 9, for generating an audible signal as will be discussed below. Output from the microprocessor is also fed to a display console 11. The display console includes a display arrangement 11a and a switch group for inputting information to the microprocessor.

The interface between the hardware, consisting of the elements 3, 5, 7, 9 and 11, and the software of the microprocessor is through input/output ports available on the microprocessor as is well known in the art. Typically, the interface will be grouped into two subsystems:

interrupt driven input/output and multiplexed or polled input/output. The former is suited to alarm conditions and consists of a battery low input and a "trigger" input, while the latter is best utilized to read the switch groups of the display console and to drive the display arrangements of the display console.

In greater detail, the power supply 7 consists of a sufficient number of rechargeable cells (typically three) to provide a voltage suitable for the electrode driver as well as an additional voltage suitable for powering a five-volt regulation system used to provide power for the microprocessor. The five-volt regulated supply may consist of a three-terminal integrated voltage regulator well known in the art. The power supply circuitry, as indicated, generates a low battery signal for use by the microprocessor.

The piezoelectric element 9 receives a drive signal directly from the microprocessor. Provisions may be made for using different tones to signal different conditions.

The display arrangement 11a consists of liquid crystal display unit arrangements. The system operates in a multiplex fashion, that is, each element of the subsystem is polled or scanned repeatedly and updated information is displayed (in the case of display) or read (in the case of the switch group) as will be further discussed with respect to FIG. 9.

In the display arrangement 11a of the display console 11, there will be a display of the time remaining (for a session) reading in minutes and seconds, an indication of a low battery, and an electrode fault indication. Average electrode current intensity will also be displayed on the display arrangement although the current intensity read-out may be either in the form of a bar graph or a numerical read-out.

The switch group includes the power ON/OFF switch (S1) and START/STOP/RESET switch (S2). This latter switch starts and stops the session. The reset function permits the user to stop the current session and to reset the machine to the (power up) state. That is, the session time is reset to 0 and the frequency of stimulation to its default value. Restarting a normally terminated session recalls previous initial session time.

The ELTEST switch (S3) allows the user to override the electrode monitoring circuitry (as will be seen below) and to generate a stimulating signal independently of whether the machine is stopped due to a bad electrode condition. The switch operates momentarily (as long as it is held) in one direction and in a toggled manner in the other.

Mode switch (S4) selects one of the following four modes:

1. Run. In this mode the machine is prepared to run on a command from the START/STOP switch.
2. Frequency set. In this mode, the stimulation frequency can be altered. The frequency is displayed on the display arrangement 11a and can be modified by pressing advance switch (S5) which is a push-button switch.
3. Session time set. This is similar to frequency set above except that the parameter being varied is session time.
4. Trigger mode. This mode allows the pulse trains to be triggered by an incoming trigger signal to the microprocessor. This circumvents the session timer. In this mode, each signal causes a new low frequency pulse (modulating, as usual, a high frequency signal) to be emitted. A single pulse for trigger input is produced of duration determined by the low frequency setting (i.e., 100 hertz frequency setting would produce a 5 msec pulse). The triggering signal can be applied to an interrupt terminal of the microprocessor as is known in the art.

The intensity of the current is set by signal amplitude potentiometer (S6).

Figure 2:
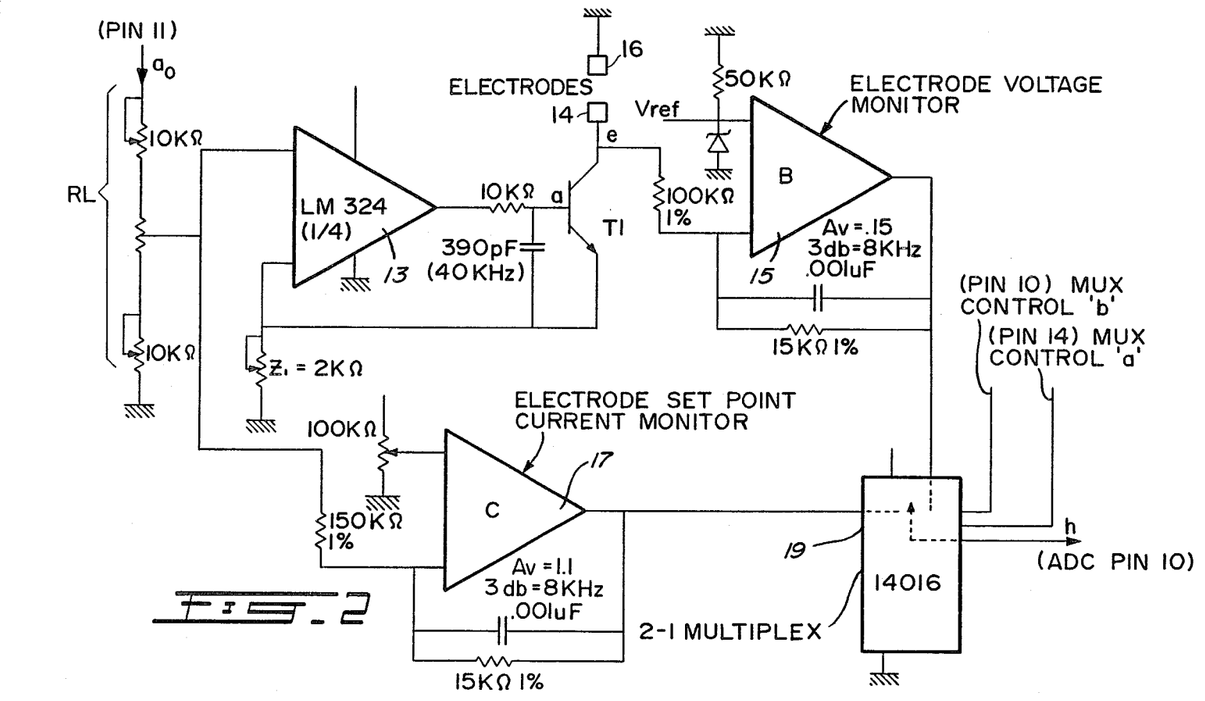
FIG. 2 is a circuit diagram of the electrode driver and monitor means.

Turning now to FIG. 2, the pulse train output from pin 11 of the microprocessor is fed to a resistance ladder RL where the amplitude is set. The set amplitude signal is then fed to the non-inverting input of operational amplifier 13. Operational amplifier 13 is set up as a non-inverting feedback amplifier. The output of operational amplifier 13 is fed to transistor T1. The base-emitter junction of the transistor T1 forms the feedback loop for the operational amplifier 13. As can be seen, one of the electrodes 14, which is placed on the patient, is connected to the collector. The other electrode, 16, is connected to ground.

The 10K resistor, between the output of 13 and the base of T1, and the 390pF capacitor, connected to the base of transistor T1, form a low pass filter to ensure gain-bandwidth product compatability. Resistance $Z_1$ determines which level of emitter current will map to the input voltage at a. The relationship is $$I_e=(V_a/Z_1)$$

Through transistor action, the collector current, and hence the electrode current, is a controlled value. The value is controlled by adjustment of resistor ladder RL through potentiometer switch (S6).

To determine whether there is a poor electrode connection, the electrode impedance is monitored. In order for the microprocessor to monitor the electrode impedance, two parameters must be known. These parameters are the electrode voltage and the electrode current. Amplifiers 15 and 17 in FIG. 2 are configured as inverting low pass amplifiers with programmable gain. They serve to average the signals present at point a (corresponds to electrode current) and point e (corresponds to electrode voltage). These signals are normalized on a 0 to 5 volt scale by the programmed feedback resistors (the 15K resistor associated with amplifier 15, and the 15K, 100K and 150K resistors associated with amplifier 17). These two outputs are fed to a 2 to 1 multiplexer 19, and the microprocessor selects one signal and then the other at the output of the multiplexer 19. The microprocessor then digitizes these values to determine if the electrode impedance is out of bounds.

The nature of the transistor T1 is such that the current in the collector will be a constant multiple ($\beta$) of the current in the base. Variations of transistor $\beta$ due to batch irregularities in temperature, etc. are compensated for by the op amp feedback loop. The 10K 390pF RC network in the base circuit serves to eliminate high frequency components of the signal which would exceed the open loop frequency response of the chip which includes the op amp 15.

It can thus be seen that the electrodes, using the electrode driver in accordance with FIG. 2, will be driven by a constant current whose amplitude is adjustable. The current will remain constant regardless of the impedance of the electrodes. Should the electrodes be short-circuited, the controlled current will continue to flow. However, the voltage across the electrodes will fall to substantially zero volts. When the electrodes are open-circuited, the voltage will rise to the magnitude of the power supply. Between these two conditions, the voltage will be a function of the electrode impedance and will be between 0 volts and the magnitude of the power supply.

Figure 3A:
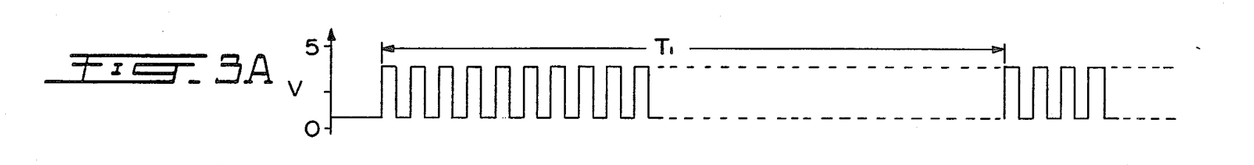
FIGS. 3A to 3C are graphs useful in describing the operation of the circuit diagram of FIG. 2.
Figure 3B:
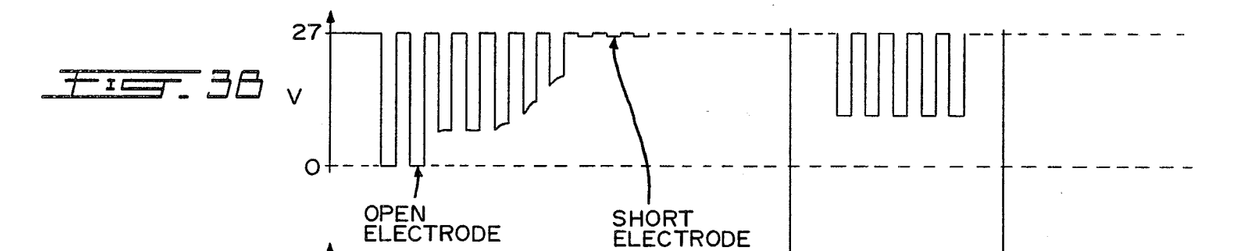

Turning now to FIGS. 3A to 3C, FIG. 3A shows the signal at the point $a_0$ in FIG. 2, that is, the pulse train from the microprocessor. FIG. 3B shows the signal at point e in FIG. 2, that is, the electrode voltage.

Figure 3C:
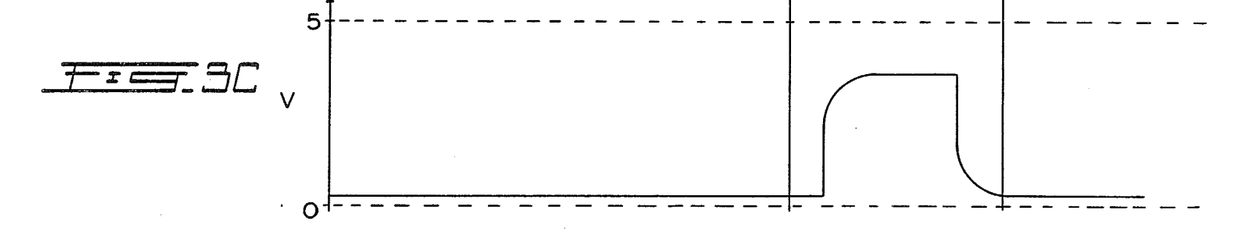

In FIG. 3B, the left-hand side gives examples of open-circuit, normal, and short-circuited electrodes. The right-hand portion shows the pulse train at the input to the monitor under normal conditions. FIG. 3C shows the signal at point h in FIG. 2. As can be seen, this is the envelope of the low frequency pulse.

Figures 4, 7:
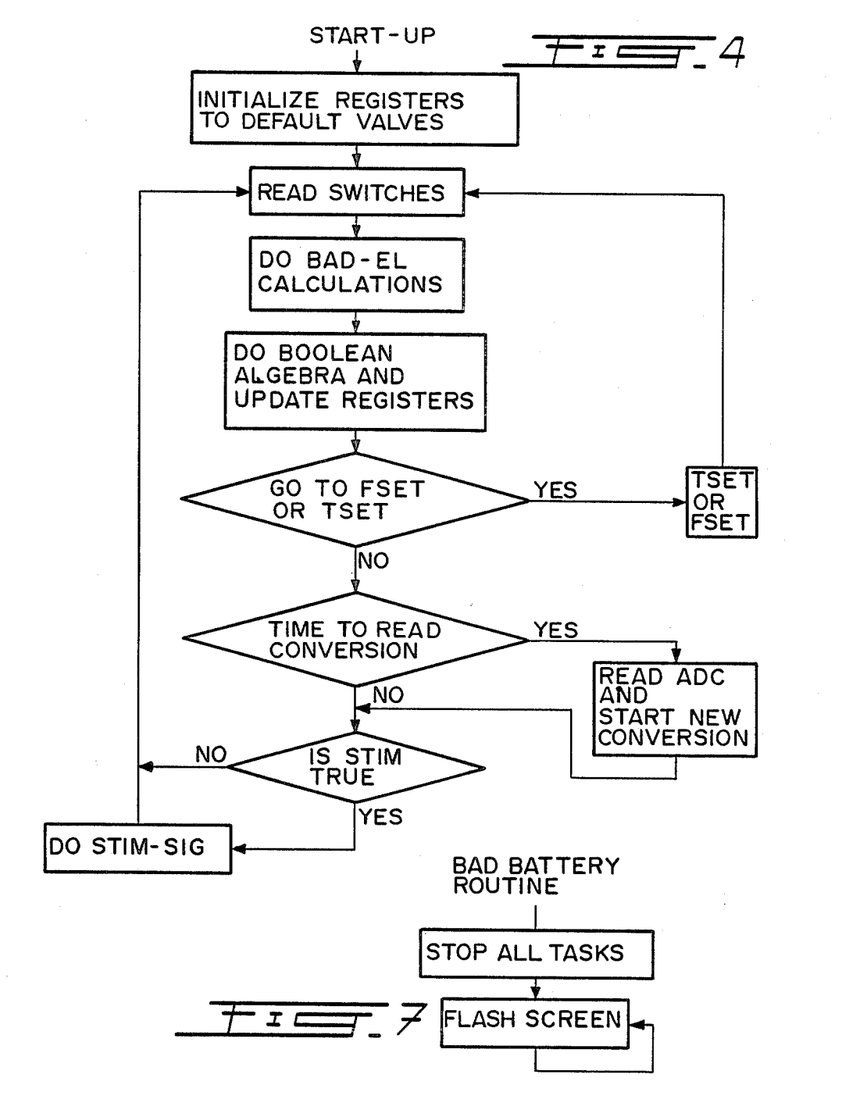
FIG. 4 is a main loop software outline of the program for controlling the microprocessor.
FIG. 7 is a flow chart of the bad battery subroutine.

Turning now to FIG. 4, after start-up, all registers are initialized to their default values. The switches are then read and a bad electrode calculation is performed. Boolean algebra calculations are performed to update the registers. If the frequency or session time is to be set, (this is determined by noting the appropriate setting of mode switch (S4)) then a reading is taken of push button switch (S5) and the registers are updated. If time or frequency are not being set, then the program asks whether it is time to read a conversion (the analog-to-digital conversion for determining poor electrode connections). If it is time to take such conversion, then a reading is taken and new conversion is started. After the above, or if it is not time to take the conversion, then the program asks whether a stimulating signal should be provided. If it should, then the stimulating signal is provided and the program returns to the read switches step. If a stimulating signal is not to be provided, then the program once again returns to the read switches step.

Figures 5, 6:
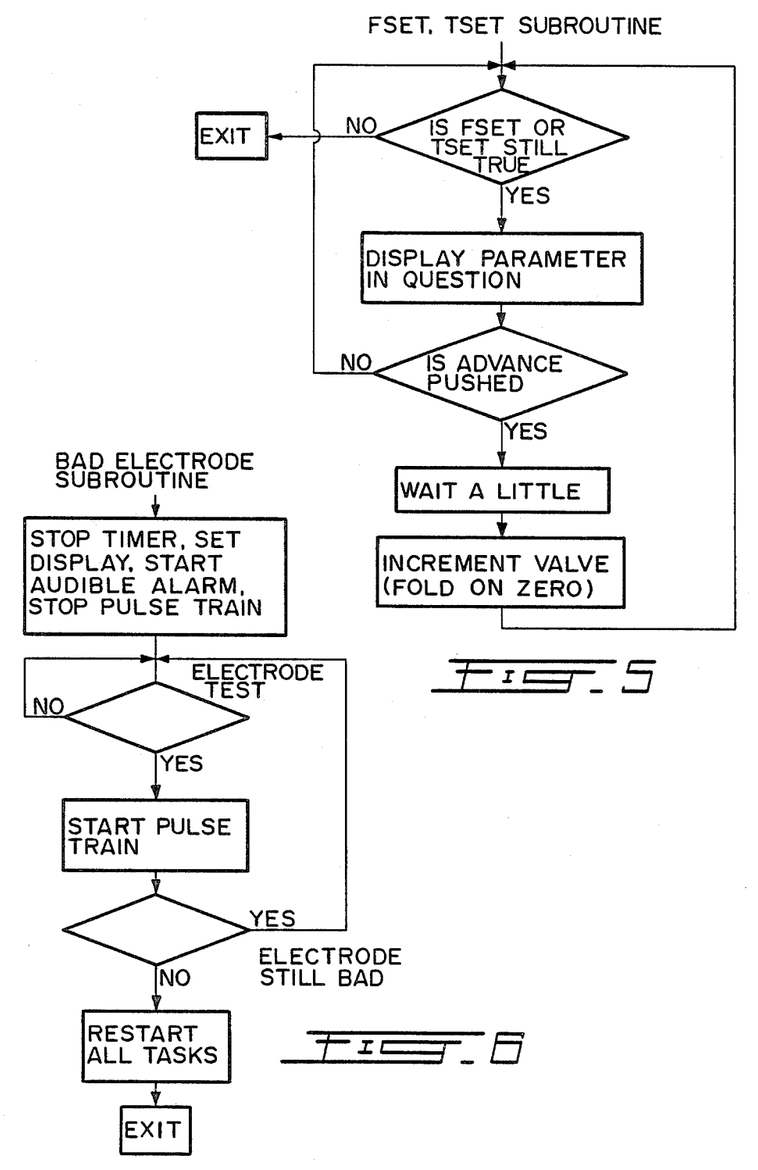
FIG. 5 is a flow chart of the frequency or time setting subroutine.
FIG. 6 is a flow chart of the bad electrode subroutine.

FIG. 5 shows a subroutine for frequency or time setting. If the instrument is in the frequency or time setting mode, the appropriate parameter is displayed. If the advance button (S5) is pushed, then, after a short period, the value is incremented and the program returns to the beginning. If the advance button is not pushed, then the program returns to the beginning of the subroutine. The subroutine is exited when the instrument is no longer in the frequency or time setting modes.

When a bad electrode is detected, the subroutine as illustrated in FIG. 6 is implemented. The timer is stopped, the display is set to indicate that there is a bad electrode, an audible alarm is started, and the pulse train is stopped. The program then queries whether (S3) is in one of the electrode test positions. If it is, a pulse train is started so that the electrode can be repositioned to attempt to obtain a proper electrode impedance. The repositioned electrode is then tested and, if the connection is still poor, the program returns to the start of the electrode test decision block. Changes can then be made to the electrode and the electrode will once again be tested. If the electrode is no longer bad, then all tests are resumed, and the subroutine is exited.

Considering now FIG. 7, if a low battery interrupt is received, all tasks are stopped and a message of low battery is flashed on the screen. There is no recovery from this interrupt until the low battery is replaced.

Figure 8:
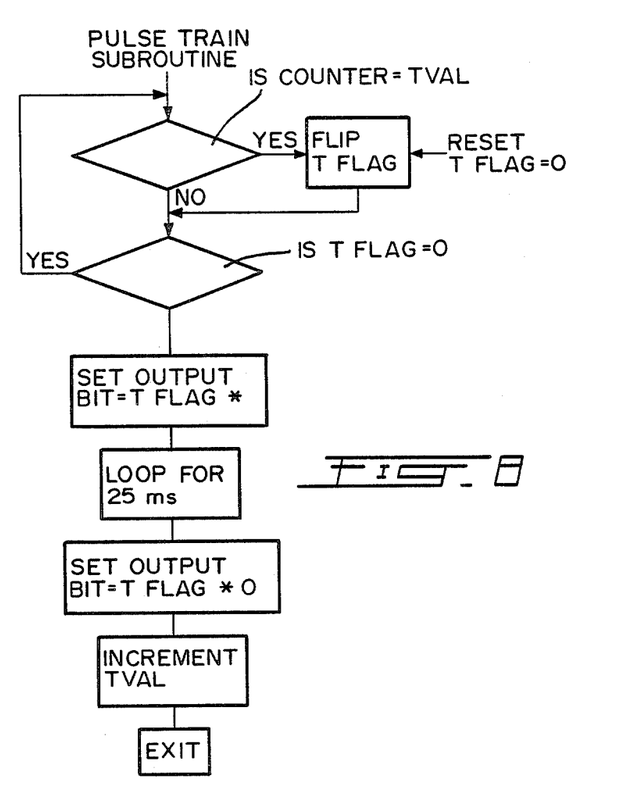
FIG. 8 is a flow chart of the pulse train subroutine.

The pulse train is generated in accordance with the flow chart illustrated in FIG. 8. In FIG. 8, the value TVAL is equal to T2. The value of T2 can be from 1 HZ to 200 HZ.

In the program illustrated in FIG. 8, the pulse train has a period of 60 microseconds so that T1 is equal to 15 KHz.

Initially, the Flip T Flag is reset so that T Flag is equal to zero. On the receipt of each pulse of the pulse train, the counter is checked to determine if the value TVAL has as yet been reached. If it has not been reached, then a check is made to determine whether T Flag is zero. When T Flag is zero, the amplitude of the low frequency pulse train is zero. When T Flag is one, the amplitude of the low frequency pulse train is one. If T Flag is equal to zero, then the program is returned to the beginning of the first counter and, when a further pulse is input, the counter is updated and compared with the TVAL.

When the counter reaches the value TVAL, T Flag is flipped so that it is set to 1, that is, the magnitude of the low frequency pulse is now 1. Thus, in the next decision block, T Flag is no longer equal to zero so that a pulse of the high frequency pulse train will be generated. This process will continue until the counter is once again equal to TVAL so that T Flag will once again be flipped to be equal to zero. Thus, it can be seen that this program generates a low frequency pulse train modulated by a high frequency pulse train. Although the high frequency pulse train generated by the present program is at a frequency of 15 KHz, the frequency of the high frequency pulse train can be varied by varying the period of the input pulse train.

In operation, the instrument works as follows:

The power is turned on and the session time and frequencies are set as is also the current intensity. The electrodes are then mounted at an appropriate place on the patient and switch (S2) is set to start whereupon a stimulating signal will be applied to the patient.

If the battery runs down, or if the electrode impedance becomes faulty, then the operation will cease and the appropriate message will be displayed on the display arrangement 11a. Corrections are then made, e.g., the batteries replaced or the electrode is corrected, and the operation is then reset. If there are no faults, then the operation will run for the session time as set and will cease when the session time has elapsed.

Although the instrument has been described as one which is maintained externally of the patient, it will of course be appreciated that a similar instrument could be internally implanted within the patient to provide direct stimulation on the nerves or spinal cord. In such a situation, all of the controls on the switch group of the console 11 would have to be applied by way of either digitally coded signals or signals of different frequencies on radio wave carriers. The signals presently applied to drive the display arrangement could be transmitted by radio wave carriers to an external display so that the status of the instrument could be examined.

In addition, the instrument has been described, as a single channel instrument. Obviously, multiple pairs of electrodes could be driven by the instrument by reconfiguring it as a multiple channel instrument.

Although particular embodiments have been described, this was for the purpose of illustrating, but not limiting, the invention. Various modifications, which will come readily to the mind of one skilled in the art, are within the scope of the invention as defined in the appended claims.

We claim:

1. A stimulator apparatus for applying a low frequency pulse train, modulating a high frequency pulse train to produce a modulated pulse train, to a patient, comprising:

electrode means for placement on said patient in the area of stimulation;

programmable microprocessor means for generating said modulated high frequency pulse train;

electrode driver means comprising means for providing an adjustable constant current to said electrode means, said means for providing an adjustable constant current comprising a constant current source having an input terminal and an output terminal, means for driving said constant current source having at least one input terminal and an output terminal and means for adjusting the amplitude of said constant current source having an input terminal and an output terminal, said modulated pulse train being fed to the input terminal of said means for adjusting the amplitude, the output terminal of said means for adjusting the amplitude being fed to said at least one input terminal of said means for driving said constant current source, the output terminal of said means for driving said constant current source being fed to the input terminal of said constant current source, and the output terminal of said constant current source being fed to said electrode means;

electrode monitor means having input and output means, the input means of said electrode monitor means being connected to the output means of said electrode driver means, the output means of said electrode monitor means being connected to an input terminal of said microprocessor means to detect poor electrode connections; and a display console enclosing said programmable microprocessor means, said electrode driver means and said electrode monitor means, and including a display arrangement and a switch group;

and wherein said means for driving said constant current source comprises a first operational amplifier having a second input terminal comprising an inverting input terminal, said at least one input terminal comprising a non-inverting input terminal;

said constant current source comprising a transistor, said input terminal of said transistor comprising a base electrode, said output terminal of said transistor comprising a collector electrode and further including an emitter electrode;

the output terminal of said first operational amplifier being connected to the base electrode of said transistor;

the collector electrode of said transistor being connected to said electrode means;

the emitter electrode of said transistor being connected to the inverting terminal of said first operational amplifier;

and wherein said electrode monitor means comprises a second operational amplifier having an inverting input terminal, a non-inverting input terminal and an output terminal, a third operational amplifier having an inverting input terminal, a non-inverting input terminal, and an output terminal, and a 2 to 1 multiplexer;

said electrode means being connected to the inverting input terminal of said second operational amplifier;

the inverting terminal of said third operational amplifier being connected to an output of said microprocessor means to receive said modulated pulse train;

the output terminals of said second and third operational amplifiers being connected to said 2 to 1 multiplexer.

2. An apparatus as defined in claim 1 and further including a power supply comprising batteries providing driving power to said programmable microprocessor means, said electrode driver means and said electrode monitor means;

low battery detector means connected to said power supply and a further interrupt terminal of said microprocessor means to detect a low battery.

3. An apparatus as defined in claim 2 and further including audible alarm means connected to an output of said programmable microprocessor means for giving an audible signal when a bad electrode connection or low battery is detected.

4. An apparatus as defined in claim 3 and further including means for setting a session time comprising selected ones of said switches of said switch group.

5. An apparatus as defined in claim 4 and including filter means between the output terminal of said first operational amplifier and the base electrode of said transistor to provide low pass filtering between said operational amplifier and said transistor.

6. An apparatus as defined in claim 1 and further including session timer means for setting the time of each session comprising selected ones of said switches of said switch group.

7. An apparatus as defined in claim 1 and further including trigger means applied to an interrupt terminal of said programmable microprocessor means to apply pulses to the patient one at a time.

* * * * *